United States Patent [19]

Turnbull

[11] Patent Number: 5,270,318
[45] Date of Patent: Dec. 14, 1993

[54] HETEROCYCLIC COMPOUNDS

[75] Inventor: Michael D. Turnbull, Reading, England

[73] Assignee: Imperial Chemical Industries PLC, London, Great Britain

[21] Appl. No.: 853,467

[22] Filed: Mar. 18, 1992

[30] Foreign Application Priority Data

Mar. 28, 1991 [GB] United Kingdom .................. 9106604
Mar. 28, 1991 [GB] United Kingdom .................. 9106606

[51] Int. Cl.$^5$ .................. A61K 31/505; C07D 239/02
[52] U.S. Cl. .................. 514/269; 544/302; 544/303; 544/304; 544/305; 544/309; 544/311; 544/312; 544/313; 544/314
[58] Field of Search .................. 544/311, 312, 313, 314, 544/319, 302, 303, 304, 305, 309; 514/269, 274

[56] References Cited

U.S. PATENT DOCUMENTS

| | | | |
|---|---|---|---|
| 3,223,707 | 12/1965 | Brokke | 544/315 |
| 4,423,047 | 12/1983 | Benneche et al. | 544/317 |
| 4,714,706 | 12/1987 | Kisida et al. | 544/316 |
| 4,791,127 | 12/1988 | Kato et al. | 544/309 |

FOREIGN PATENT DOCUMENTS 36839 9/1991 European Pat. Off. .

Primary Examiner—Cecilia Tsang
Attorney, Agent, or Firm—Joel G. Ackerman

[57] ABSTRACT

A compounds of formula (I):

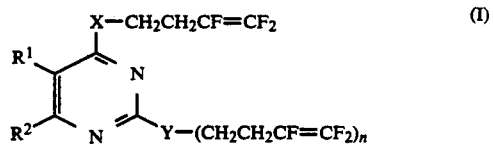

wherein $R^1$ and $R^2$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^4R^5$, hydroxy, acylamino, $-CO_2R^3$, $-O(CH_2)_mCO_2R^3$, phenyl, phenoxy, benzyl or benzyloxy, the phenyl group or phenyl moiety of the benzyl group being optionally substituted in the ring; or $R^1$ and $R^2$ when taken together form a 5- or 6-membered ring; m is 1 or 2; $R^3$ and $R^5$ are hydrogen or $C_{1-4}$alkyl; $R^4$ is $C_{1-4}$alkyl; n is 0 or 1; X is oxygen or sulphur; Y is hydrogen when n is 0; or Y is oxygen or sulphur when n is 1; are useful as nematicides.

13 Claims, No Drawings

HETEROCYCLIC COMPOUNDS

The present invention relates to novel pyrimidine derivatives having nematicidal activity, to processes for their preparation, to compositions containing them, and to methods for killing or controlling nematode pests using them.

U.S. Pat. No. 3,223,707 describes certain 2-(trifluorobutenylmercapto)-pyrimidine derivatives having nematicidal properties.

According to the present invention there is provided a compound of formula (I) wherein $R^1$ and $R^2$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^4R^5$, hydroxy, acylamino, $-CO_2R^3$, $-O(CH_2)_mCO_2R^3$, phenyl, phenoxy, benzyl or benzyloxy, the phenyl group or phenyl moiety of the benzyl group being optionally substituted in the ring; or $R^1$ and $R^2$ when taken together form a 5- or 6-membered ring; m is 1 or 2; $R^3$ and $R^5$ are hydrogen or $C_{1-4}$alkyl; $R^4$ is $C_{1-4}$alkyl; n is 0 or 1; X is oxygen or sulphur; Y is hydrogen when n is 0; or Y is oxygen or sulphur when n is 1.

When either of $R^1$ or $R^2$ is an alkyl group it can be straight or branched chain and is preferably $C_{1-4}$alkyl, in particular ethyl, propyl, isopropyl, n-butyl, iso-butyl, sec-butyl or tertiary butyl.

When either of $R^1$ or $R^2$ is an alkenyl or alkynyl group it can be straight or branched chain and preferably contains up to 6 carbon atoms, for example, allyl or propargyl.

When either of $R^1$ or $R^2$ is a phenyl, phenoxy, benzyl or benzyloxy group, the phenyl moiety may be optionally substituted with halogen, (for example, chlorine or fluorine), cyano, alkyl, haloalkyl, alkoxy or haloalkoxy, the alkyl group being preferably $C_{1-4}$alkyl and the alkoxy group being preferably $C_{1-6}$alkyl. Examples of such groups are 2-, 3- or 4-fluorophenyl, 2-, 3- or 4-chlorophenyl, 2,4- or 2,6-difluorophenyl, 2,4-or 2,6-dichlorophenyl, 2-chloro-4-fluorophenyl, 2-chloro-6-fluorophenyl, 2-fluoro-4-chlorophenyl, 2-fluoro-6-chlorophenyl, 2-, 3- or 4-methoxyphenyl, 2, 4-dimethoxyphenyl, 2-, 3-, or 4-ethoxyphenyl, 2-, 3- or 4-methylphenyl, 2-, 3- or 4-ethylphenyl, 2-, 3- or 4-trifluoromethylphenyl, and the corresponding ring substituted benzyl, phenoxy and benzyloxy groups.

When either of $R^1$ or $R^2$ is a cycloalkyl or alkylcycloalkyl group, it preferably contains from 3 to 7 carbon atoms, for example, cyclopropyl, cyclopentyl, cyclohexyl or methylcyclopropyl.

When either of $R^1$ or $R^2$ is halogen, it is preferably fluorine or chlorine.

When either of $R^1$ or $R^2$ is haloalkyl, the alkyl moiety is preferably $C_{1-4}$alkyl, for example, trifluoromethyl, trifluoroethyl or pentafluoroethyl.

When either of $R^1$ or $R^2$ is an alkoxy, alkenoxy or alkoxyalkyl group, it can be straight or branched chain and preferably contains up to 6 carbon atoms, for example, methoxy, ethoxy, propoxy, butoxy, butenoxy, methoxymethyl, methoxyethyl or ethoxymethyl.

When either of $R^1$ or $R^2$ is a haloalkoxy group, it can be straight or branched chain and preferably contains up to 6 carbon atoms, for example, trifluoromethoxy, trifluoroethoxy or pentafluoroethoxy.

When either of $R^1$ or $R^2$ is an alkylthio group, the alkyl preferably contains up to 4 carbon atoms. For example, -S-methyl, -S-ethyl, -S-propyl, S-butyl.

When either of $R^1$ or $R^2$ is $NR^5R^6$, it is preferably $NHCH_3$, $N(CH_3)_2$ or $N(C_2H_5)_2$.

When either of $R^1$ or $R^2$ is acylamino, it is preferably $NHCOCH_3$ or $NCOC_2H_5$.

When either of $R^1$ or $R^2$ is $CO_2R^4$, $R^4$ is preferably hydrogen, methyl or ethyl.

When either of $R^1$ or $R^2$ is $O(CH_2)_mCO_2R^4$, m is preferably 2 and $R^4$ is preferably hydrogen, methyl or ethyl.

When $R^1$ and $R^2$ are taken together to form a 5- or 6-membered ring, it is preferably a carbocyclic ring, for example, $-(CH_2)_3-$, $-(CH_2)_4-$ or $-CH=CH-CH=CH-$.

Of particular interest are the compounds of formula (I) where $R^1$ and $R^2$ are independently hydrogen, $C_{1-4}$alkyl or $C_{1-4}$haloalkyl, X is oxygen, Y is sulphur and n is 1. Or alternately, the compounds of formula (I) where $R^1$ and $R^2$ are independently hydrogen, $C_{1-4}$alkyl or $C_{1-4}$haloalkyl, X and Y are both sulphur and n is 1. Or in a further alternative, the compounds of formula (I) where $R^1$ and $R^2$ are independently hydrogen, $C_{1-4}$alkyl or $C_{1-4}$haloalkyl, X is oxygen, Y is hydrogen and n is 0.

Examples of the compounds of formula (I) are set out in Table I.

TABLE I

| COMPOUND NO. | $R^1$ | $R^2$ | X | Y | n |
|---|---|---|---|---|---|
| 1 | H | H | O | S | 1 |
| 2 | H | n-$C_3H_7$ | O | S | 1 |
| 3 | H | H | S | S | 1 |
| 4 | H | $CF_3$ | O | S | 1 |
| 5 | H | $CH(CH_3)_2$ | O | S | 1 |
| 6 | $-(CH_2)_4-$ | | O | S | 1 |
| 7 | H | $CF_3$ | O | H | 0 |
| 8 | H | $CH_3$ | S | S | 1 |
| 9 | H | Cl | S | S | 1 |
| 10 | H | $CH_2CH=CH_2$ | S | S | 1 |
| 11 | H | C≡CH | S | S | 1 |
| 12 | H | $^cC_3H_5$ | S | S | 1 |
| 13 | H | 1-$CH_3-_cC_3H_5$ | S | S | 1 |
| 14 | H | $CF_3$ | S | S | 1 |
| 15 | H | CN | S | S | 1 |
| 16 | H | OH | S | S | 1 |
| 17 | $C_2H_5$ | H | S | S | 1 |
| 18 | $CH(CH_3)_2$ | H | S | S | 1 |
| 19 | F | F | S | S | 1 |
| 20 | H | $CH_3$ | O | S | 1 |
| 21 | H | Cl | O | S | 1 |
| 22 | H | $CH_2CH=CH_2$ | O | S | 1 |
| 23 | H | C≡CH | O | S | 1 |
| 24 | H | $^cC_3H_5$ | O | S | 1 |
| 25 | H | 1-$CH_3-^cC_3H_5$ | O | S | 1 |
| 26 | Cl | $CF_3$ | O | S | 1 |
| 27 | H | CN | O | S | 1 |
| 28 | H | OH | O | S | 1 |
| 29 | $C_2H_5$ | H | O | S | 1 |
| 30 | $CH(CH_3)_2$ | H | O | S | 1 |
| 31 | F | F | O | S | 1 |
| 32 | H | $CH_3$ | S | O | 1 |
| 33 | $CH_3$ | H | S | O | 1 |
| 34 | Cl | H | S | O | 1 |
| 36 | $-(CH_2)_3-$ | | S | O | 1 |
| 37 | $-CH=CH-CH=CH-$ | | S | S | 1 |
| 38 | $-CH=CH-CH=CH-$ | | O | S | 1 |

The compounds of formula (I) when X, Y, n, $R^1$ and $R^2$ have the meanings defined above are prepared by reacting a correspondingly substituted pyrimidine of formula (II) with 4-bromo-trifluorobut-1-ene in the presence of a base such as a carbonate, for example, potassium carbonate, and an inert solvent, for example dimethylformamide. Both the compounds of formula (II) and 4-bromo-trifluorobut-1-ene can be obtained by conventional methods or from commercial sources.

Thus, according to a further aspect of the present invention there is provided a process for the preparation of compounds of formula (I) wherein $R^1$, $R^2$, X, Y and n have the meanings defined above which comprises reacting a correspondingly substituted compound of formula (II) with 4-bromo-trifluorobut-1-ene in the presence of a base.

The compounds of formula (I) where either of $R^1$ or $R^2$ is alkoxy can alternatively be prepared by reacting the correspondingly hydroxy derivative of formula (I) with an alkylating agent, for example dimethyl sulphate.

Thus, according to a yet further aspect of the present invention there is provided a process for the preparation of compounds of formula (I) wherein $R^1$, $R^2$, X, Y and n have the meanings defined above, provided that at least one of $R^1$ or $R^2$ is alkoxy, which comprises reacting a corresponding hydroxy derivative of formula (I) with an alkylating agent.

The compounds of formula (I) are nematicidal and can be used to control nematodes in crop plants. Therefore, in a further aspect of the invention, there is provided a method for killing or controlling nematodes which comprises applying to the locus of the pests or to a plant susceptible to attack by the pest an effective amount of a compound of formula (I) as defined herein.

The term "controlling" extends to non-lethal effects which result in the prevention of damage to the host plant and the limitation of nematode population increase. These effects may be the result of chemical induced disorientation, immobilisation, or hatch prevention or induction. The chemical treatment may also have deleterious effects on nematode development or reproduction.

The compounds of the invention can be used against both plant-parasitic nematodes and nematodes living freely in the soil. Examples of plant-parasitic nematodes are: ectoparasites, for example Xiphinema spp., Longidorus spp. and Trichodorous spp.; semi-endoparasites, for example, Tylenchulus spp.; migratory endoparasites, for example, Pratylenchus spp., Radopholus spp. and Scutellonema spp.; sedentary endoparasites, for example, Heterodera spp., Globodera spp. and Meloidogyne spp.; and stem and leaf endoparasites, for example, Ditylenchus spp., Aphelenchoides spp. and Hirshmaniella spp.

The compounds of the invention can also be used in combating a range of insects and acarids. Examples include Lepidoptera, Diptera, Homoptera and Coleoptera (including Diabrotica i.e. corn rootworms).

In order to apply the compound to the locus of the nematode or to a plant susceptible to attack by the nematode, the compound is usually formulated into a composition which includes in addition to the compound of formula (I) suitable inert diluent or carrier materials, and/or surface active agents. Thus in a further aspect of the invention there is provided a nematicidal composition comprising an effective amount of a compound of formula (I) as defined herein and an inert diluent or carrier material and optionally a surface active agent.

The amount of composition generally applied gives a rate of active ingredient from 0.01 to 10 kg per hectare, preferably from 0.1 to 6 kg per hectare.

The compositions can be applied to the soil, plant or seed, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or CS) for use in seed treatments. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

g) Organochlorine compounds such as benzene hexachloride, DDT, chlordane or dieldrin;

i) Amidines, such as chlordimeform or amitraz;

j) Fumigant agents.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The following Examples illustrate the invention. The compounds were identified and characterised by means of the melting points, nuclear magnetic resonance spectroscopy ($^1$H NMR $\delta$ (CDCl$_3$)), or mass spectroscopy.

EXAMPLE 1

This example illustrates the preparation of Compound No. 1 of Table I. 2-Thiouracil (4 g), 4-bromo-1,1,2-trifluorobut-1-ene (4.31 g) and potassium carbonate (2.16 g) were placed together in 60 ml of dimethylformamide, stirred and heated to 120° C.

After 2 hours at 120° C. the reaction mixture was allowed to cool, then poured into 100 ml of water and extracted with ethyl acetate, (3×30 ml). The combined organic extracts were washed with water, dried over anhydrous magnesium sulphate, filtered and concentrated under reduced pressure to yield a yellow oil. The oil was subjected to chromatography using silica eluted with ethyl acetate/hexane (3:17) to yield 0.56 g (10%) of a yellow oil.

Compound No. 1 NMR: 2.63–2.86 (m,4H); 3.28 (t,2H); 4.51 (t,2H); 6.42 (d,1H); 8.23 (d,1H). M+: 344

Preparation of Compound No. 2 of Table I was carried out by analogy with the preparation of Compound No. 1 of Table I.

Compound No. 2 NMR: 0.95 (t,3H); 1.60–1.80 (m,2H); 2.55 (t,2H); 2.68–2.88 (m,4H); 3.30 (t,2H); 4.50 (t,2H); 6.28 (s,1H)

EXAMPLE 2

This example illustrates the preparation of Compound No. 3 of Table I. Dithiouracil (2 g), 4-bromo-1,1,2-trifluorobut-1-ene (2.63 g) and potassium carbonate (0.96 g) were placed together in 30 ml of acetone, stirred and heated to reflux.

After 2 hours at reflux the reaction mixture was allowed to cool, then filtered to remove insoluble potassium salts. The filtrate was concentrated under reduced pressure to yield a brown solid. The solid was subjected to chromatography using silica eluted with ethyl acetate/hexane (3:17) to yield 1.86 g (37%) of a yellow oil.

NMR: 2.63–2.84 (m,4H); 3.25–3.42 (m,4H); 6.68 (d,1H); 8.15 (d,1H)

M+: 360

Coumpound No. 37 was prepared by analogy with the preparative route of Example 2.

NMR: 2.7–2.9 (m, 4H), 3.4 (t, 2H), 3.5 (t, 2H), 7.5–7.6 (m, 2H), 7.78 (dd, 1H)

Melting point: 38.2–39.1

EXAMPLE 3

This example illustrates the preparation of Compound No. 4 of Table I. 4-Hydroxy-2-mercapto-6-trifluoromethylpyrimidine (5 g), 4-bromo-1,1,2-trifluorobut-1-ene (4.82 g) and potassium carbonate (1.77 g) were placed together in 80 ml of acetone and heated to reflux.

After 2½ hours at reflux the reaction mixture was allowed to cool, then filtered to remove insoluble potassium salts. The filtrate was evaporated under reduced pressure to yield an off-white oil. The oil was subjected to chromatography using silica eluted with ethyl acetate/hexane (1:9) to yield a white solid (0.28 g, 2%).

MNR: 2.67–2.87 (m,4H), 3.31 (t,2H), 4.58 (t,2H), 6.77 (s,1H)

M+: 412

EXAMPLE 4

This Example illustrates the preparation of Compound No. 5 of Table I.

Sodium metal (2.9 g) and methanol (80 ml) were stirred together, causing the methanol to reflux gently. After 2 hours thiourea (4.8 g) was added.

The reaction was heated gently to maintain reflux and ethyl isobutyryl acetate (10 g) was added dropwise in 20 ml of methanol.

After 4 hours the rection was allowed to cool and the solvents removed under reduced pressure. The residue was poured into 100 ml of water, extracted with 50 ml of diethyl ether, and the organic layer was discarded. The aqueous layer was acidified with 2M Hydrochloric acid and extracted with ethyl acetate (1×100 ml, 1×50 ml). The combined organic extracts were dried over anhydrous MgSO4, filtered and the solvent evaporated under reduced pressure to yield a yellow solid. This solid was subjected to chromatography using silica and ethyl acetate/hexane (1:1) as the eluent yielding a white solid (5.0 g, 46%).

The white solid, 4-Hydroxy-2-mercapto-6-isopropyl-pyrimidine, was then used to prepare Compound No. 5 of Table I without further purification using the method (by analogy) of Example 2.

NMR: 1.26 (d,6H), 2.67–2.93 (m,5H), 3.28 (t,2H), 4.49 (t,2H), 6.27 (s,1H)

M+: 386

Compound No. 6 was prepared from ethyl 2-cyclohexanone carboxylate (by analogy) using the method of Example 4.

Compound No. 6

NMR: 1.70–1.88 (m,4H), 2.50 (t,2H), 2.68–2.88 (m,6H), 3.25 (t,2H), 4.50 (t,2H)

M+: 398

EXAMPLE 5

In order to illustrate the nematicidal properties of the compounds of formula (I), compounds from Table I were tested on root knot nematodes and cyst nematodes.

Methodology

Test A: Tomato plants (6–8 weeks old, variety 'Moneymaker') were planted out into soil infested with second stage juveniles of the root knot nematode *Meloidogyne incognita*. The soil was drenched with a composition of a compound of formula (I) (obtained by diluting 1 part of a solution of the compound in a 1:1 mixture of acetone and ethanol with 99 parts of water containing 0.05% of a wetting agent) at a rate of 2.5 or 1.25 ppm in a drench volume of 200 ml/kg of soil. The roots of the plants were examined after 3 weeks to determine the percentage reduction in the number of root knots compared with a control treatment omitting the compound. There were 3 replicates per treatment.

Test B: Tomato plants (6–8 weeks old, variety 'Moneymaker') were transplanted into soil infested with potato cyst nematode (*Globodera rostochiensis*). The soil was drenched with a composition of a compound of formula (I) (obtained by diluting 1 part of a solution of the compound in a 1:1 mixture of acetone and ethanol with 99 parts of water containing 0.05% of a wetting agent) at a rate of 10 ppm in a drench volume of 266 ml/kg of soil. The cysts were extracted from the soil after 8 weeks by flotation and percentage reduction in the number of cysts compared with a control treatment omitting the compound was determined. There were 5 replicates per treatment.

The results are given in Table II. In the table a blank indicates less than 25% reduction, a hyphen indicates no test carried out at that rate.

TABLE II

| | % ROOT KNOT REDUCTION | | | % CYST REDUCTION | |
| --- | --- | --- | --- | --- | --- |
| | APPLICATION RATE (PPM) | | | | |
| COMPOUND NO. | 40 | 2.5 | 1.25 | 20 | 10 |
| 1 | 99 | 99 | 84 | — | 95 |
| 3 | 100 | 85 | | 100 | — |
| 37 | 99 | | | 57 | — |

The compounds of formula (I) display nematicidal activity against different types of nematodes including the cyst nematode. A further advantage is that the compounds are not phytotoxic to the target plant. Very little phytotoxicity was observed in the above tests. This is a particularly desirable feature when treating young plants and seeds.

The following examples demonstrate formulations suitable for applying the compounds of the present invention. The amount of ingredient is expressed in parts by weight or grams per liter as indicated. A * indicates a trademark.

EXAMPLE 6

This example demonstrates granules suitable for soil application. The granules can be made be standard techniques such as impregnation, coating, extrusion or agglomeration.

| | | % w/w |
|---|---|---|
| Impregnated granule: | Active ingredient | 5 |
| | Wood Rosin | 2.5 |
| | Gypsum granules (20–40 mesh) | 92.5 |
| Coated granule: | Active ingredient | 0.5 |
| | 'Solvesso'* 200 | 0.4 |
| | Calcium carbonate granules (30–60 mesh) | 99.1 |
| Slow release granule: | Active ingredient | 10 |
| | Polyvinylacetate/vinyl chloride copolymer latex | 5 |
| | Attapulgus granules | 85 |

EXAMPLE 7

This example demonstrates formulations for use as a spray. The compounds can be formulated as wettable powders, water dispersible granules, suspension concentrates, emulsifiable concentrates, emulsions or microcapsule suspensions for application diluted in water.

| | | g/l |
|---|---|---|
| Emulsifiable concentrate: | Active ingredient | 250 |
| | Calcium dodecylbenzene sulphonate | 50 |
| | Nonyl phenol ethoxylate | 50 |
| | Alkylbenzene solvent | to 1 liter |

| | | % w/w |
|---|---|---|
| Wettable powder: | Liquid active ingredient | 40 |
| | lignosulphonate dispersant | 5 |
| | silica | 25 |
| | sodium lauryl sulphate | 3 |
| | china clay (kaolin) | 27 |
| Microcapsule suspension: | Liquid active ingredient | 250 |
| | toluene diisocyanate | 10 |
| | polymethylene polyphenyl isocyanate | 20 |
| | nonyl phenol ethoxylate | 6 |
| | lignosulphonate dispersant | 15 |
| | xanthan gum | 1 |
| | bentonite | 10 |
| | biocide 'Proxel'* | 0.1 |
| | sodium carbonate | 5 |
| | water | to 1 liter |

The microcapsule suspensions can be used as a spray, soil drench or as an intermediate to prepare slow release granules for application to the soil.

| | | g/l |
|---|---|---|
| Suspension concentrate: | Solid active ingredient | 400 |
| | lignosulphonate dispersant | 50 |
| | sodium lauryl sulphate | 30 |
| | xanthan gum | 1 |
| | biocide 'Proxel'* | 0.1 |
| | bentonite | 10 |
| | water | to 1 liter |

EXAMPLE 8

This example demonstrates formulations suitable for use as seed treatments in conventional application machinery.

| | | % w/w |
|---|---|---|
| Dry seed treatment: | Active ingredient | 20 |
| | dodecyl benzene | 3 |
| | Rubine Toner (dyestuff) | 2.7 |
| | Talc | 53.3 |
| | Silica | to 100% |

The suspension concentrate and microcapsule suspension of Example 4 can be used as flowable concentrates for seed treatment.

EXAMPLE 9

This example demonstrates the formulation of the compounds for electrostatic spraying.

| | g/l |
|---|---|
| Active ingredient | 200 |
| N-methylpyrollidone | 50 |
| Soyabean oil | 120 |
| 'Solvesso'* 200 | to 1 liter |

CHEMICAL FORMULAE
(corresponding to formulae numbers in description)

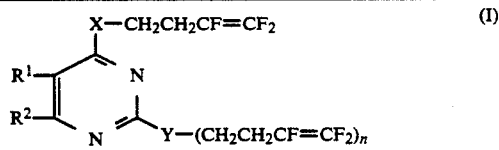  (I)

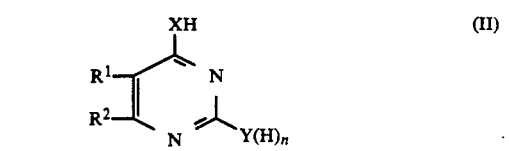  (II)

I claim:
1. A compound of formula (I):

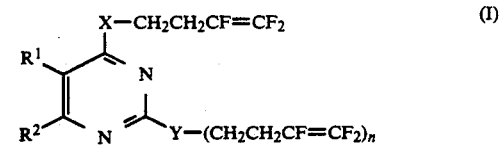  (I)

wherein $R^1$ and $R^2$ are independently hydrogen, $C_{1-4}$ alkyl, $C_{2-6}$ alkenyl, $C_{2-6}$ alkynyl, $C_{3-7}$ cycloalkyl or alkylcycloalkyl, halogen, $C_{1-4}$ haloalkyl, $C_{1-6}$ alkoxy, $C_{2-6}$ alkenoxy, $C_{2-6}$ alkoxyalkyl, $C_{1-6}$ haloalkoxy, $C_{1-4}$ alkylthio, cyano, nitro, amino, $NR^4R^5$, hydroxy, $C_{2-3}$ acylamino, $-CO_2R^3$, $-O(CH_2)_mCO_2R^3$, phenyl, phenoxy, benzyl or benzyloxy; or $R^1$ and $R^2$ when taken together with the adjacent carbon atoms form a 5- or 6-membered carbocyclic ring; m is 1 or 2; $R^3$ and $R^5$ are hydrogen or $C_{1-4}$ alkyl; $R^4$ is $C_{1-4}$ alkyl; n is 1; X is oxygen or sulphur; and Y is oxygen or sulphur.

2. A compound according to claim 1 wherein $R^1$ and $R^2$ are independently hydrogen, alkyl, alkenyl, alkynyl, halogen, haloalkyl, alkoxy, haloalkoxy, alkylthio or hydroxy.

3. A compound according to claim 1 wherein $R^1$ and $R^2$ are independently hydrogen, $C_{1-4}$ alkyl, $C_{1-4}$ haloalkyl, $C_{1-6}$ alkoxy, chlorine or fluorine.

4. A compound according to claim 1 wherein $R^1$ and $R^2$ are independently phenyl, phenoxy, benzyl or benzyloxy.

5. A compound according to claim 1 wherein $R^1$ and $R^2$ taken together form a 5- or 6-membered carbocylic ring.

6. A compound according to claim 1 wherein both X and Y are sulphur.

7. A compound according to claim 1 wherein X is oxygen, and Y is sulphur.

8. A compound according to claim 1 wherein $R^1$ and/or $R^2$ is hydrogen.

9. A compound according to claim 1 wherein $R^1$ and $R^2$ are independently hydrogen, $C_{1-4}$ alkyl or $C_{1-4}$ haloalkyl, X is oxygen, and Y is sulphur.

10. A compound according to claim 1 wherein $R^1$ and $R^2$ are independently hydrogen, $C_{1-4}$ alkyl or $C_{1-4}$ haloalkyl, and X and Y are both sulphur.

11. A compound according to claim 1 wherein both $R^1$ and $R^2$ are hydrogen.

12. A nematicidal composition comprising an effective amount of a compound of formula (I) as defined in any one of claims 1 to 11 and an inert diluent or carrier material and optionally a surface active agent.

13. A method for killing or controlling nematode pests which comprises applying to the locus of the pests or to a plant susceptible to attack by the pest an effective amount of a compound of formula (I) as defined in any one of claims 1 to 11.

* * * * *